(12) United States Patent
Johnsen et al.

(10) Patent No.: US 11,547,393 B2
(45) Date of Patent: Jan. 10, 2023

(54) ENDOSCOPE SYSTEM

(71) Applicant: AMBU A/S, Ballerup (DK)

(72) Inventors: Lasse Markworth Johnsen, Birkerød (DK); Jesper Mads Bartroff Frederiksen, Vedbæk (DK)

(73) Assignee: AMBU A/S, Ballerup (DK)

( * ) Notice: Subject to any disclaimer, the term of this patent is extended or adjusted under 35 U.S.C. 154(b) by 651 days.

(21) Appl. No.: 16/610,410

(22) PCT Filed: May 2, 2018

(86) PCT No.: PCT/DK2018/050089
§ 371 (c)(1),
(2) Date: Nov. 1, 2019

(87) PCT Pub. No.: WO2018/202268
PCT Pub. Date: Nov. 8, 2018

(65) Prior Publication Data
US 2022/0233178 A1     Jul. 28, 2022

(30) Foreign Application Priority Data

May 2, 2017    (DK) .......................... PA 2017 70295
May 2, 2017    (DK) .......................... PA 2017 70296
(Continued)

(51) Int. Cl.
*A61B 1/00*      (2006.01)
*A61B 10/02*     (2006.01)
(Continued)

(52) U.S. Cl.
CPC ...... *A61B 10/0283* (2013.01); *A61B 1/00045* (2013.01); *A61B 1/00068* (2013.01);
(Continued)

(58) Field of Classification Search
CPC ............ A61B 10/0096; A61B 1/00045; A61B 1/00068; A61B 1/00114; A61B 1/00128;
(Continued)

(56) References Cited

U.S. PATENT DOCUMENTS

| 4,643,197 A | 2/1987 | Greene et al. |
| 4,760,838 A | 8/1988 | Fukuda |

(Continued)

FOREIGN PATENT DOCUMENTS

| CN | 1177742 C | 12/2004 |
| CN | 1864750 A | 11/2006 |

(Continued)

OTHER PUBLICATIONS

International Search Report and Written Opinion from corresponding Application No. PCT/DK2018/050089, dated Sep. 5, 2018.
(Continued)

*Primary Examiner* — Timothy J Neal
*Assistant Examiner* — Sung Ham
(74) *Attorney, Agent, or Firm* — Faegre Drinker Biddle & Reath LLP

(57) ABSTRACT

An endoscope system for delivering a fluid to a patient and retrieving for diagnostic purposes from the patient a specimen. The system includes an endoscope, a fluid container containing a fluid, and a first specimen container for receiving a specimen. The endoscope system has a first user selectable state and a second user selectable state, where the endoscope system in the first user selectable state is configured to automatically deliver the fluid from the fluid container to the patient and in the second user selectable state is configured to automatically retrieve a specimen from the patient and provide the specimen to the first specimen container.

21 Claims, 3 Drawing Sheets

(30) Foreign Application Priority Data

May 2, 2017 (DK) .............................. PA 2017 70297
May 2, 2017 (DK) .............................. PA 2017 70298

(51) Int. Cl.
| | |
|---|---|
| *A61B 90/00* | (2016.01) |
| *A61B 1/015* | (2006.01) |
| *A61B 1/267* | (2006.01) |
| *A61B 1/31* | (2006.01) |
| *A61B 10/00* | (2006.01) |

(52) U.S. Cl.
CPC ...... *A61B 1/00114* (2013.01); *A61B 1/00128* (2013.01); *A61B 1/015* (2013.01); *A61B 1/2676* (2013.01); *A61B 1/31* (2013.01); *A61B 10/0045* (2013.01); *A61B 90/06* (2016.02); *A61B 2010/0225* (2013.01)

(58) Field of Classification Search
CPC ......... A61B 1/015; A61B 1/2676; A61B 1/31; A61B 10/04; A61B 90/06; A61B 1/307; A61B 1/00091; A61B 1/00121; A61B 10/06; A61B 1/00016; A61B 2217/007; A61B 2217/005
See application file for complete search history.

(56) References Cited

U.S. PATENT DOCUMENTS

| | | | |
|---|---|---|---|
| 5,039,198 | A | 8/1991 | Van Beek |
| 5,312,332 | A | 5/1994 | Bales et al. |
| 5,800,414 | A | 9/1998 | Cazal |
| 7,065,940 | B2 | 6/2006 | Dudek et al. |
| 7,172,579 | B2 | 2/2007 | Barzell et al. |
| 7,479,257 | B2 | 1/2009 | Nguyen et al. |
| 8,974,399 | B2 | 3/2015 | Teixeira et al. |
| 9,339,172 | B2 | 5/2016 | Slenker et al. |
| 9,808,146 | B2 | 11/2017 | Furlong |
| 9,943,291 | B2 | 4/2018 | VanderWoude et al. |
| 10,046,288 | B2 | 8/2018 | Wang et al. |
| 11,357,386 | B2 | 6/2022 | Lund et al. |
| 2003/0167053 | A1 | 9/2003 | Taufig |
| 2003/0216617 | A1* | 11/2003 | Hirakui ................. A61B 1/015 |
| | | | 600/118 |
| 2005/0054995 | A1 | 3/2005 | Barzell et al. |
| 2006/0047185 | A1 | 3/2006 | Shener et al. |
| 2006/0224042 | A1 | 10/2006 | Jackson et al. |
| 2006/0258955 | A1 | 11/2006 | Hoffman et al. |
| 2007/0027359 | A1* | 2/2007 | Salman ................. A61B 1/015 |
| | | | 600/158 |
| 2007/0043262 | A1* | 2/2007 | Levy ................. A61B 1/00068 |
| | | | 600/156 |
| 2008/0255424 | A1 | 10/2008 | Durgin et al. |
| 2011/0169260 | A1 | 7/2011 | Lin et al. |
| 2011/0245606 | A1 | 10/2011 | Hayashi et al. |
| 2012/0089164 | A1* | 4/2012 | Kojima ............. A61B 17/3203 |
| | | | 606/167 |
| 2012/0095369 | A1 | 4/2012 | Teixeira et al. |
| 2013/0079702 | A1* | 3/2013 | Klein .................... A61M 1/774 |
| | | | 604/22 |
| 2014/0088460 | A1 | 3/2014 | Teixeira et al. |
| 2014/0121560 | A1* | 5/2014 | Parks ..................... A61B 10/02 |
| | | | 600/562 |
| 2014/0187859 | A1 | 7/2014 | Leeuw et al. |
| 2015/0018711 | A1* | 1/2015 | Furlong ............. A61B 10/0275 |
| | | | 600/565 |
| 2015/0182105 | A1* | 7/2015 | Salman ............. A61B 1/00137 |
| | | | 600/104 |
| 2015/0327875 | A1 | 11/2015 | Look et al. |
| 2016/0220102 | A1 | 8/2016 | Shener-Irmakoglu et al. |

FOREIGN PATENT DOCUMENTS

| | | |
|---|---|---|
| CN | 101242780 A | 8/2008 |
| CN | 1920530 B | 10/2012 |
| CN | 1957837 B | 10/2012 |
| CN | 103153199 A | 6/2013 |
| CN | 101616699 B | 1/2014 |
| CN | 204932566 U | 1/2016 |
| CN | 104379051 B | 2/2017 |
| CN | 104220016 B | 6/2018 |
| CN | 104114204 B | 10/2018 |
| EP | 0 637 436 A1 | 5/1993 |
| EP | 0 890 339 A1 | 1/1999 |
| EP | 2 105 087 A1 | 9/2009 |
| EP | 2 476 365 A1 | 7/2012 |
| WO | WO 2004/020019 A2 | 3/2004 |
| WO | WO 2005/097250 A1 | 10/2005 |
| WO | WO 2006/039646 A2 | 4/2006 |
| WO | WO 2006/124489 A1 | 11/2006 |
| WO | WO 2007/050516 A2 | 5/2007 |
| WO | WO 2008/124779 A1 | 10/2008 |
| WO | WO 2008/137234 A1 | 11/2008 |
| WO | WO 2010/065214 A2 | 6/2010 |
| WO | WO 2014/070525 A1 | 5/2014 |
| WO | 2018059642 A2 | 4/2018 |

OTHER PUBLICATIONS

Search Report from corresponding Danish Application No. PA 2017 70295, dated Aug. 31, 2017.
Search Report from corresponding Danish Application No. PA 2017 70296, dated Jul. 4, 2017.
Search Report from corresponding Danish Application No. PA 2017 70297, dated Sep. 12, 2017.
Search Report from corresponding Danish Application No. PA 2017 70298, dated Aug. 25, 2017.
First examination report in Chinese application No. 201880033401. 3, dated Dec. 27, 2021, with translation.
International Preliminary Report on Patentability received for PCT Patent Application No. PCT/DK2018/202268, dated Nov. 14, 2019, 12 pages.
International Search Report and Written Opinion received for PCT Patent Application No. PCT/DK2018/202268, dated Sep. 5, 2018, 16 pages.
European search report of European Application No. 18 723 402.6, dated Jul. 6, 2022, 6 pages.

* cited by examiner

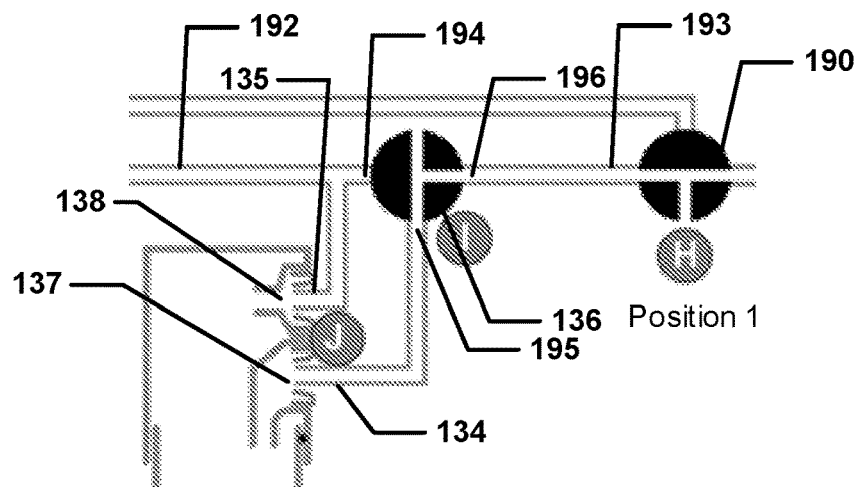
Fig. 3a
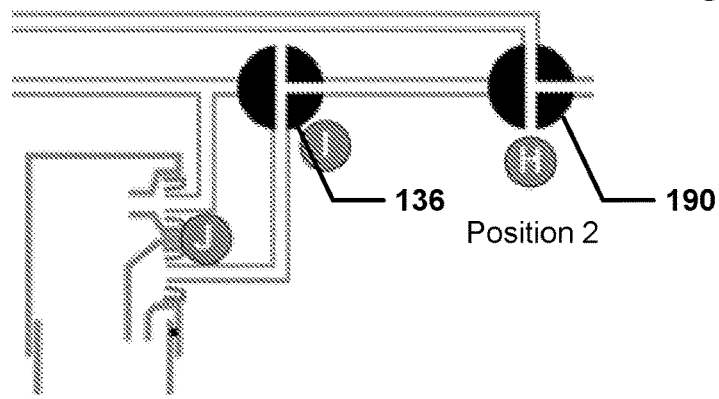
Fig. 3b
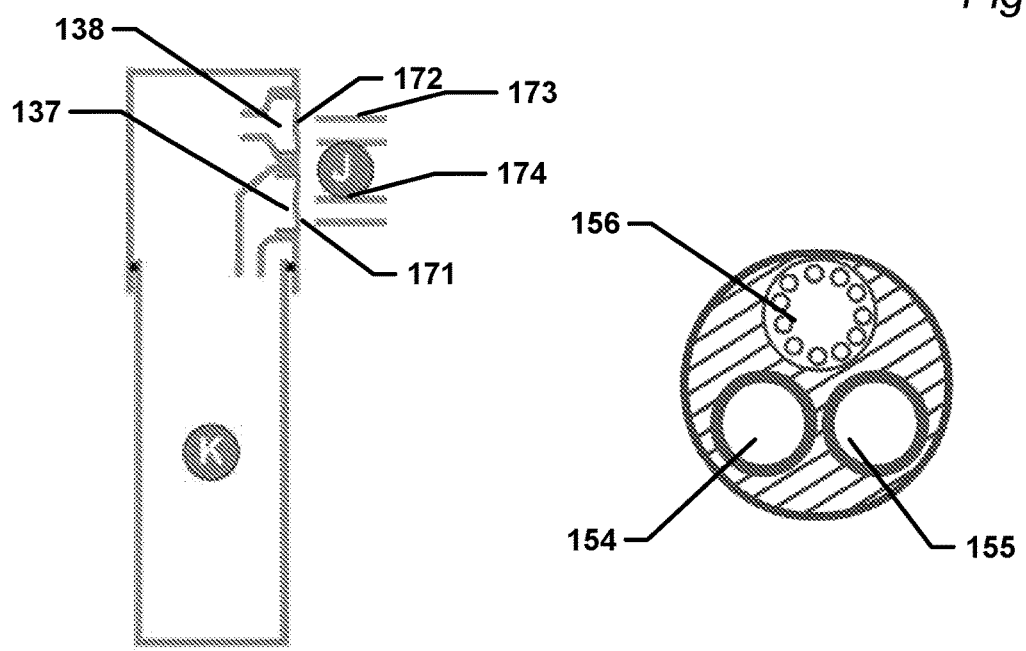
Fig. 3c
Fig. 4

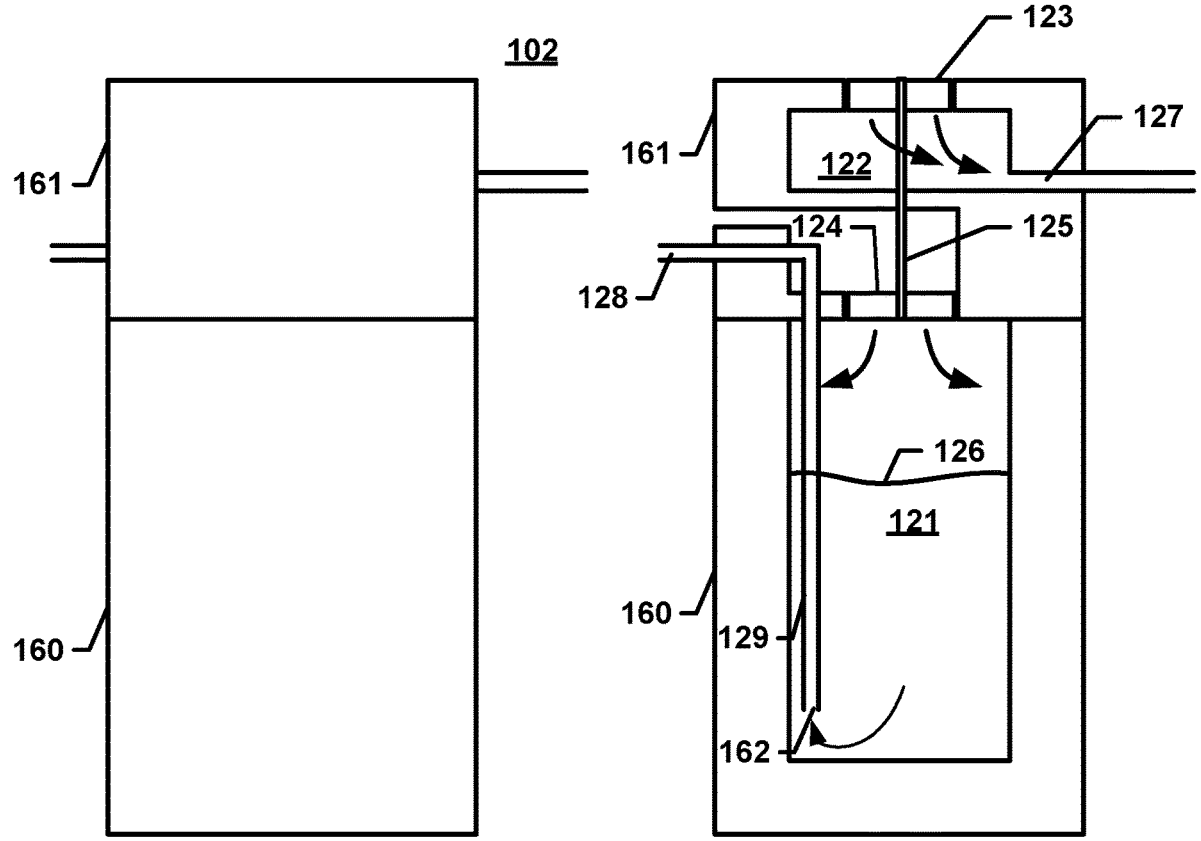
*Fig. 5a*  *Fig. 5b*

ENDOSCOPE SYSTEM

CROSS-REFERENCE TO RELATED APPLICATIONS

This application is a National stage application filed under 35 U.S.C. § 371 of International Application No. PCT/DK2018/050089, filed on May 2, 2018, which claims the benefit of Denmark Patent Applications Nos. PA 2017 70295, PA 2017 70296, PA 2017 70297, and PA 2017 70298, said Denmark applications filed on May 2, 2017, and all said applications incorporated herein by reference thereto.

FIELD

The present invention relates to an endoscope system for delivering a fluid to a patient and/or retrieving for diagnostic purposes from the patient a specimen, devices for use in such systems, and use of such devices and system for medical procedures.

BACKGROUND

Such endoscope systems are used in procedures such as bronchial lavage (BL), Bronchial wash (BW), or bronchoalveolar lavage (BAL) which are commonly used procedures for obtaining specimens of organic material from a lung segment of a patient. This is basically done by flushing a lung segment with sterile water and then sucking the water into a sample container. More specifically the distal end of an endoscope is advanced to the location in the lung where the sample is to be taken. In bronchoalveolar lavage, the distal end is then pressed into firm engagement against the interior of the lung, i.e. a wedge position, to help securing the position in a process commonly referred to as wedging.

Via the working channel of the endoscope, sterile water, e.g. a 0.9% saline solution, is instilled into the lung at the sample location and as much as possible extracted again, now containing organic material, and thus constituting a specimen. Typically, this is done by attaching a filled syringe of a volume between 20 ml and 60 ml, e.g. 50 ml to the working channel of the endoscope, via a communication port in endoscope handle and emptying the syringe. The attached syringe may then be used for the subsequent extraction. This process is normally repeated several times in a row with new syringes or refiling of the used syringe, e.g. three to four, the specimens being suitable for various purposes, depending which number of specimens in the sequence they are, because the composition of the organic material varies. Upon extraction the content is transferred to a suitable container that normally is labelled accordingly.

As an alternative to the extraction using the syringe, the extraction may be performed using an external suction and a Lukens trap, e.g. as disclosed in U.S. Pat. No. 4,643,197.

However, handling syringes and Lukens traps is complex and may require a number of medical care givers to collaborate. Furthermore, the medical care givers may risk getting into contact with contagious material when handling the syringes or Lukens traps, e.g. each time the medical care givers mounts Lukens traps/syringes, remove Lukens traps/syringes, each time the Lukens trap/syringe is removed from the current endoscope scope system etc.

Thus, it remains a problem to provide an endoscope system that is simpler and more safe to use.

SUMMARY

According to a first aspect the invention relates to an endoscope system for delivering a fluid to a patient and retrieving for diagnostic purposes from the patient a specimen, comprising an endoscope, a fluid container containing a fluid, and a first specimen container for receiving a specimen, wherein:

said endoscope comprises a proximal end and a distal end, a handle at the proximal end and an insertion tube extending from the proximal end towards the distal end, the insertion tube comprising an internal working channel extending from the handle to the distal end of the insertion tube;

said fluid container being connectable to said endoscope handle;

said first specimen container being connectable to said endoscope handle and a suction device;

wherein said endoscope system has a first user selectable state and a second user selectable state, wherein said endoscope system in said first user selectable state is configured to automatically deliver the fluid from said fluid container to the patient through said internal working channel and in said second user selectable state is configured to automatically retrieve a specimen through said insertion tube from the patient and provide the specimen to said first specimen container.

Consequently, by having an endoscope system configured to both automatically deliver a fluid and retrieve a specimen, a system that is safe and simple to use is provided.

The endoscope may be an endoscope configured to be introduced into any body cavity, such as into the airways of a patient, e.g. a bronchoscope. The endoscope system may be adapted for used in procedures such as bronchial lavage (BL), Bronchial wash (BW), or bronchoalveolar lavage (BAL). The fluid of the fluid container may be sterile water such as a saline solution or a saline like solution e.g. a 0.9% saline solution. The fluid container may be configured to store at least 100 ml, 200 ml, or 500 ml fluid. The fluid container may be connectable to the endoscope handle via a cable connecting the fluid container to the endoscope handle. The first specimen container may be connectable to the endoscope handle via a cable connecting the first specimen container to the endoscope handle. Alternatively, the first specimen container may be connectable to the endoscope handle via another device connected to the first specimen container e.g. a specimen dock, where the other device is connected to the endoscope handle via a cable. Correspondingly, the first specimen container may be connectable to the suction device via a cable connecting the first specimen container to the suction device. Alternatively, the first specimen container may be connectable to the suction device via another device connected to the first specimen container e.g. a specimen dock, where the other device is connected to the suction device via a cable. The suction device may be a wall suction device present in a medical care facility. The suction device may be utilized to suck the specimen e.g. a part of the fluid delivered from the fluid container mixed with body fluids, from the distal end of the insertion tube when the endoscope system is in the second user selectable state. As an example, the suction device may be connected to the insertion tube via the endoscope handle and the first specimen container. The specimen may be retrieved from the patient via the internal working channel. The system may further comprise a pump configured to pump the fluid from the fluid container into the internal working channel when the system is in the first user selectable state. The fluid container may be pressurized e.g. the fluid container may be provided with a pump configured to pressurize the fluid container.

In some embodiments, said endoscope handle comprises a first button wherein the activation of said first button sets said endoscope system in said first user selectable state or said second user selectable state.

The first button may be movable between a first position where it is in a passive state and a second position where it is in an active state i.e. the movement from the first position to the second position activates to first button. The first button may be activated in a first manner and in a second manner where the activation of the first button in the first manner sets said endoscope system in said first user selectable state and the activation of said first button in said second manner sets said endoscope system in said second user selectable state. Alternatively, the activation of the first button may change the current state of the system e.g. so that a first activation sets the system in the first user selectable state, a second activation sets the system in the second user selectable state, and a third activation sets the system in a passive state.

In some embodiments, said endoscope handle comprises a first button and a second button, and wherein the activation of said first button sets said endoscope system in said first user selectable state and the activation of said second button sets said endoscope system in said second user selectable state.

In some embodiments, said fluid container is configured to be pressurized, said handle comprises a first valve for opening and closing for a fluid flow from said fluid container to the distal opening of said working channel; and a second valve for opening and closing for a fluid flow from said distal end of said working channel to said first specimen container, and wherein the activation of said first button opens said first valve and the activation of said second button opens said second valve.

In some embodiments, the system further comprises one or more flow meters configured to measure the amount of fluid delivered from the fluid container and/or the amount of fluid retrieved from distal end of said working channel.

In some embodiments, the endoscope system further comprises a processing unit and a display, and wherein the flow meter is communicatively connectable to the processing unit, and the processing unit is communicatively connectable to the display and configured to control the display to show information related to the amount of fluid delivered and/or retrieved.

In some embodiments, the endoscope system further comprises a specimen dock configured to hold said first specimen container, said specimen dock comprising a main inlet for receiving the specimen, a main outlet, a specimen channel having a first specimen outlet and a first suction inlet, and a first specimen valve having a first position and a second position;

wherein said first specimen container has a specimen inlet and a suction outlet, the specimen inlet of the first specimen container is connectable to the first specimen outlet of the specimen dock, the suction outlet of the first specimen container is connectable to the first suction inlet of the specimen dock, the main inlet of the specimen dock is connectable to said endoscope handle, said main outlet of the specimen dock is connectable to said suction device; and wherein said first specimen valve in said first position is configured to guide the specimen flowing in the specimen channel out of said first specimen outlet, and said specimen first valve in said second position is configured to block the first specimen outlet and guide the specimen flowing in the specimen channel further downstream in the specimen channel.

Consequently, by having a specimen dock the specimen container may be securely handled limiting the exposure to contagious diseases for the medical personal.

The main inlet of the specimen dock may be connectable to said endoscope handle via a cable connecting the endoscope handle to the main inlet of the specimen dock. Alternatively, the specimen dock may be directly connected to the endoscope handle. The first specimen valve may have an operational element such as a knob or a leaver for allowing a user to move the specimen valve to the first or the second position. In some embodiments, the specimen inlet and the suction outlet of the first specimen container may be formed by a single opening in the first specimen container adapted for receiving a part of the specimen dock having two channels.

In some embodiments, said specimen channel is connected to said main inlet and said main outlet, the first specimen valve has an inlet, a first outlet, and a second outlet, the inlet of the first specimen valve is connected to a first part of the specimen channel, the first outlet of the first specimen valve is connectable to the specimen inlet of the first specimen container, the second outlet of the first specimen valve is connected to a second part of the specimen channel, and wherein when said first specimen valve is in said first position the first outlet of the first specimen valve is open and the second outlet of the first specimen valve is closed, and when said first specimen valve is in said second position the first outlet of the first specimen valve is closed and the second outlet of the first specimen valve is open.

In some embodiments, the endoscope system further comprises a second specimen container connectable to said endoscope handle, said specimen dock being further configured to hold said second specimen container, said specimen channel further have a second specimen outlet, a second suction inlet, and a second specimen valve having a first position and a second position;

wherein said second specimen container has a specimen inlet and a suction outlet, the specimen inlet of the second specimen container is connectable to the second specimen outlet of the specimen dock, the suction outlet of the second specimen container is connectable to the second suction inlet of the specimen dock, and wherein said second specimen valve in said first position is configured to guide the specimen flowing in the specimen channel downstream from said first specimen valve out of said second specimen outlet, and said specimen valve in said second position is configured to block the second specimen outlet and guide the specimen flowing in the specimen channel further downstream in the specimen channel.

Consequently, a plurality of specimens may be collected in a simple and secure manner.

The second specimen valve may have an operational element such as a knob or a leaver for allowing a user to move the specimen valve to the first or the second position.

In some embodiments, the second specimen valve has an inlet, a first outlet, and a second outlet, the inlet of the second specimen valve is connected to the second part of the specimen channel, the first outlet of the second specimen valve is connectable to the specimen inlet of the second specimen container, the second outlet of the second specimen valve is connected to a third part of the specimen channel, and wherein when said second specimen valve is in said first position the first outlet of the second specimen valve is open and the second outlet of the second specimen valve is closed, and when said second specimen valve is in said second position the first outlet of the second specimen valve is closed and the second outlet of the second specimen valve is open.

In some embodiments, said first specimen container can be attached and detached from said specimen dock, and wherein said specimen inlet and/or said suction outlet is/are configured to automatically close when said first specimen container is detached from said specimen dock to prevent a specimen stored in said specimen container to exit said specimen container through said specimen inlet and/or said suction outlet.

Consequently, the first specimen container may be safely handled after being detached from the specimen dock.

In some embodiments, said specimen dock further comprises a bypass channel and a bypass valve having a first position and a second position;

wherein said bypass valve in said first position is configured to guide the specimen through the bypass channel and out of the main outlet, and said bypass valve in said second position is configured to guide the specimen into said specimen channel.

Consequently, the medical personal may in an easy and safe manner control the point in time when a specimen is taken.

The bypass valve may have an operational element such a knob or a leaver for allowing a user to move the valve to the first or the second position.

The first specimen valve, the second specimen valve, and/or the bypass valve may be configured to be controlled remotely from the specimen dock e.g. using one or more control elements on the endoscope handle and/or using one or more control elements of other parts of the system. As an example a control element e.g. a button, arranged on the endoscope handle may be mechanically coupled to the first specimen valve, the second specimen valve, or the bypass valve e.g. via a wire, and when actuated configured to move said valve from the first position to the second position and/or from the second position to the first position e.g. the endoscope handle may be provided with three control elements one for each valve. Alternatively, the specimen dock may comprise an actuator configured to move the first specimen valve, the second specimen valve, and/or the bypass valve from the first position to the second position and/or from the second position to the first position in response to activation of a control element communicatively coupled to the actuator e.g. a physical button on the endoscope handle or a button on a touch screen. In some embodiments, said bypass valve has an inlet, a first outlet, and a second outlet, the inlet of the bypass valve is connected to said main inlet, the first outlet of the bypass valve is connected to the bypass channel, the second outlet of the bypass valve is connected to the first part of the specimen channel, and the bypass channel is connected to said main outlet; and wherein when said bypass valve is in said first position the first outlet of the bypass valve is open and the second outlet of the bypass valve is closed, and when said bypass valve is in said second position the first outlet of the bypass valve is closed and the second outlet of the bypass valve is open.

In some embodiments, the endoscope system further comprises a pump configured to draw air into the fluid container through an air inlet of the fluid container thereby creating over pressure in said fluid container that can be used to propel the fluid stored in said first chamber out of a fluid outlet of the fluid container and into a patient via the endoscope handle.

The pump may use any energy source such as electrical energy or a manual pressure applied by a user e.g. the pump may be a hand-driven manual pump that is used before a procedure to create an over-pressure in the fluid container.

In some embodiments, said fluid container has a first chamber and a second chamber, a turbine, a fan, and a mechanical coupling, wherein said fluid is stored in said first chamber, said second chamber being sealed off from said first chamber, said mechanical coupling couples said turbine with said fan so that a rotation of said turbine results in a rotation of said fan, wherein said second chamber has an air inlet and a suction outlet, said suction outlet being connectable to a suction device, said turbine being arranged in said air inlet and being configured to rotate when air is flowing through said air inlet into said second chamber, said first chamber having an air inlet and a fluid outlet, wherein said fluid outlet is connectable to the endoscope handle, said fan is arranged in said air inlet and being configured to draw air into the first chamber when being rotated, whereby when said suction outlet is connected to said suction device an under pressure is created in said second chamber drawing air into said second chamber through said air inlet resulting in a rotation of said turbine and through said mechanical coupling a rotation of said fan, the rotation of said fan drawing air into said first chamber creating an over pressure in said first chamber that can be used to propel the fluid stored in said first chamber out of said fluid outlet and into the patient via the endoscope handle.

Consequently, a suction device such as the wall suction present in most hospital operating rooms may be used as an energy source to propel the fluid from the fluid container.

In some embodiments, said fluid container comprises a bottom element and a top element, the top element comprising said second chamber and said turbine, said top element being connectable to said bottom element, and said top element and said bottom element together forms said first chamber.

Consequently, by having most of the parts of the fluid container in the top element, the bottom element may be exchanged if more fluid is needed.

In some embodiments, said top element further comprises said fan 124.

In some embodiments, said fluid container further comprises a suction channel having a proximal end, a distal end, and a suction channel fluid inlet, wherein the distal end of the suction channel is adapted to extend into said fluid stored in said first chamber, said suction channel fluid inlet being formed at said distal end of the suction channel and the fluid outlet of the first chamber being formed at said proximal end of said suction channel.

In some embodiments, the endoscope system further comprises a connection cable for connecting said endoscope handle with said fluid container and said first specimen container, wherein said connection cable has a proximal end and one or more distal ends, the proximal end being connectable to said endoscope handle and the one or more distal ends being connectable to said fluid container and said first specimen container, wherein said connection cable has a first part extending from said proximal end towards said one or more distal ends, wherein said connection cable comprises a suction channel for connecting the first specimen container with the endoscope handle and a fluid channel for connecting the fluid container with the endoscope handle wherein the suction channel and the fluid channel is connected and forms a multi-lumen cable in said first part of the connection cable.

This makes it easier to setup the system for use. Furthermore, by having a multi-lumen cable the number of cables connected to the endoscope handle may be reduced thereby making movement of the endoscope less restricted.

In some embodiments, the connection cable has a first distal end, a second distal end, and a second part extending from said first part towards the first distal end and the second distal end, wherein the suction channel and the fluid channel splits into a first sub cable and a second sub cable in said second part of the connection cable.

In some embodiments, the connection cable further comprises one or more signal cables for connecting the endoscope handle with a signal receiving unit (display, storage unit, communication unit, camera unit), wherein the one or more signal cables are connected to the suction channel and the fluid channel in said first part of the connection cable.

The signal receiving unit may be a display, a storage unit, a communication unit, or a camera unit. The endoscope may comprise a camera arranged at the distal end of the insertion tube and wherein the signal receiving unit is a display or a communication unit. Alternatively, the insertion tube may comprise optical fibres and wherein the signal receiving unit is a camera.

In some embodiments, the connection cable further has a third distal end, the second part extends from said first part towards the first distal end, the second distal end, and the third distal end wherein the suction channel, the fluid channel, and the one or more signal cables splits into a first sub cable, a second sub cable, and a third sub cable in said second part of the connection cable.

In some embodiments, the endoscope system further comprises a suction splitter having a suction outlet, a first suction inlet and a second suction inlet, wherein the suction outlet is connectable to the suction device, the first suction inlet is connectable to the first specimen container and the second suction inlet is connectable to the suction outlet of the second chamber of the fluid container.

According to a second aspect the invention relates to use of an endoscope system as disclosed in relation to the first aspect of the invention for a bronchial lavage (BL), procedure, a bronchoalveolar lavage (BAL) procedure, Bronchial wash (BW) procedure, or a colonoscopy procedure on a human or animal subject.

According to a third aspect the invention relates to an endoscope system for delivering a fluid to a patient, comprising an endoscope, a fluid container containing a fluid, wherein:

said endoscope comprises a proximal end and a distal end, a handle at the proximal end and an insertion tube extending from the proximal end towards the distal end, the insertion tube comprising an internal working channel extending from the handle to the distal end of the insertion tube;

said fluid container being connectable to said endoscope handle;

wherein said endoscope system has a first user selectable state, wherein said endoscope system in said first user selectable state is configured to automatically deliver the fluid from said fluid container to the patient through said internal working channel.

In some embodiments, said endoscope handle comprises a first button, and wherein the activation of said first button sets said endoscope system in said first user selectable state.

In some embodiments, said fluid container is configured to be pressurized.

In some embodiments, said handle comprises a first valve for opening and closing for a fluid flow from said fluid container to the distal opening of said working channel; and wherein the activation of said first button opens said first valve.

In some embodiments, the endoscope system further comprises a pump configured to draw air into the fluid container through an air inlet of the fluid container thereby creating over pressure in said fluid container that can be used to propel the fluid stored in said first chamber out of a fluid outlet of the fluid container and into a patient via the endoscope handle.

In some embodiments, said fluid container has a first chamber and a second chamber, a turbine, a fan, and a mechanical coupling, wherein said fluid is stored in said first chamber, said second chamber being sealed off from said first chamber, said mechanical coupling couples said turbine with said fan so that a rotation of said turbine results in a rotation of said fan, wherein said second chamber has an air inlet and a suction outlet, said suction outlet being connectable to a suction device, said turbine being arranged in said air inlet and being configured to rotate when air is flowing through said air inlet into said second chamber, said first chamber having an air inlet and a fluid outlet, wherein said fluid outlet is connectable to the endoscope handle, said fan is arranged in said air inlet and being configured to draw air into the first chamber when being rotated, whereby when said suction outlet is connected to said suction device an under pressure is created in said second chamber drawing air into said second chamber through said air inlet resulting in a rotation of said turbine and through said mechanical coupling a rotation of said fan, the rotation of said fan drawing air into said first chamber creating an over pressure in said first chamber that can be used to propel the fluid stored in said first chamber out of said fluid outlet and into the patient via the endoscope handle.

In some embodiments, said fluid container comprises a bottom element and a top element, the top element comprising said second chamber and said turbine, said top element being connectable to said bottom element, and said top element and said bottom element together forms said first chamber.

In some embodiments, said top element further comprises said fan.

In some embodiments, said fluid container further comprises a suction channel having a proximal end, a distal end, and a suction channel fluid inlet, wherein the distal end of the suction channel is adapted to extend into said fluid stored in said first chamber, said suction channel fluid inlet being formed at said distal end of the suction channel and the fluid outlet of the first chamber being formed at said proximal end of said suction channel.

According to a fourth aspect the invention relates to a fluid container for use with an endoscope system for delivering a fluid to a patient, wherein said fluid container has a first chamber and a second chamber, a turbine, a fan, and a mechanical coupling, wherein said fluid is stored in said first chamber, said second chamber being sealed off from said first chamber, said mechanical coupling couples said turbine with said fan so that a rotation of said turbine results in a rotation of said fan, wherein said second chamber has an air inlet and a suction outlet, said suction outlet being connectable to a suction device, said turbine being arranged in said air inlet and being configured to rotate when air is flowing through said air inlet into said second chamber, said first chamber having an air inlet and a fluid outlet, wherein said fluid outlet is connectable to an endoscope handle of said endoscope system, said fan is arranged in said air inlet and being configured to draw air into the first chamber when being rotated, whereby when said suction outlet is connected to said suction device an under pressure is created in said second chamber drawing air into said second chamber through said air inlet resulting in a rotation of said turbine and through said mechanical coupling a rotation of said fan, the rotation of said fan drawing air into said first chamber creating an over pressure in said first chamber that can be used to propel the fluid stored in said first chamber out of said fluid outlet and into a patient via the endoscope handle.

According to a fifth aspect the invention relates to use of an endoscope system as disclosed in relation to the third aspect or a fluid container as disclosed in relation to the fourth aspect for a bronchial lavage (BA) procedure, a bronchoalveolar lavage (BAL) procedure, or a colonoscopy procedure on a human or animal subject.

According to a sixth aspect the invention relates to an endoscope system for delivering a fluid to a patient and retrieving for diagnostic purposes from the patient a specimen, comprising an endoscope, and a first specimen container for receiving a specimen, wherein:

said endoscope comprises a proximal end and a distal end, a handle at the proximal end and an insertion tube extending from the proximal end towards the distal end, the insertion tube comprising an internal working channel extending from the handle to the distal end of the insertion tube;

said first specimen container being connectable to said endoscope handle and a suction device;

wherein said endoscope system further comprising a specimen dock configured to hold said first specimen container, said specimen dock comprising a main inlet for receiving the specimen, a main outlet, a specimen channel having a first specimen outlet and a first suction inlet, and a first specimen valve having a first position and a second position;

wherein said first specimen container has a specimen inlet and a suction outlet, the specimen inlet of the first specimen container is connectable to the first specimen outlet of the specimen dock, the suction outlet of the first specimen container is connectable to the first suction inlet of the specimen dock, the main inlet of the specimen dock is connectable to said endoscope handle, said main outlet of the specimen dock is connectable to said suction device; and wherein said first specimen valve in said first position is configured to guide the specimen flowing in the specimen channel out of said first specimen outlet, and said specimen valve in said second position is configured to block the first specimen outlet and guide the specimen flowing in the specimen channel further downstream in the specimen channel.

In some embodiments, said specimen channel is connected to said main inlet and said main outlet, the first specimen valve has an inlet, a first outlet, and a second outlet, the inlet of the first specimen valve is connected to a first part of the specimen channel, the first outlet of the first specimen valve is connectable to the specimen inlet of the first specimen container, the second outlet of the first specimen valve is connected to a second part of the specimen channel, and wherein when said first specimen valve is in said first position the first outlet of the first specimen valve is open and the second outlet of the first specimen valve is closed, and when said first specimen valve is in said second position the first outlet of the first specimen valve is closed and the second outlet of the first specimen valve is open.

In some embodiments, said endoscope system further comprises a second specimen container connectable to said endoscope handle, said specimen dock being further configured to hold said second specimen container, said specimen channel further have a second specimen outlet, a second suction inlet, and a second specimen valve having a first position and a second position;

wherein said second specimen container has a specimen inlet and a suction outlet, the specimen inlet of the second specimen container is connectable to the second specimen outlet of the specimen dock, the suction outlet of the second specimen container is connectable to the second suction inlet of the specimen dock, and wherein said second specimen valve in said first position is configured to guide the specimen flowing in the specimen channel downstream from said first specimen valve out of said second specimen outlet, and said specimen valve in said second position is configured to block the second specimen outlet and guide the specimen flowing in the specimen channel further downstream in the specimen channel.

In some embodiments, the second specimen valve has an inlet, a first outlet, and a second outlet, the inlet of the second specimen valve is connected to the second part of the specimen channel, the first outlet of the second specimen valve is connectable to the specimen inlet of the second specimen container, the second outlet of the second specimen valve is connected to a third part of the specimen channel, and wherein when said second specimen valve is in said first position the first outlet of the second specimen valve is open and the second outlet of the second specimen valve is closed, and when said second specimen valve is in said second position the first outlet of the second specimen valve is closed and the second outlet of the second specimen valve is open.

In some embodiments, said first specimen container can be attached and detached from said specimen dock, and wherein said specimen inlet and/or said suction outlet is/are configured to automatically close when said first specimen container is detached from said specimen dock to prevent a specimen stored in said specimen container to exit said specimen container through said specimen inlet and/or said suction outlet.

In some embodiments, said specimen dock further comprises a bypass channel and a bypass valve having a first position and a second position;

wherein said bypass valve in said first position is configured to guide the specimen through the bypass channel and out of the main outlet, and said bypass valve in said second position is configured to guide the specimen into said specimen channel.

In some embodiments, said bypass valve has an inlet, a first outlet, and a second outlet, the inlet of the bypass valve is connected to said main inlet, the first outlet of the bypass valve is connected to the bypass channel, the second outlet of the bypass valve is connected to the first part of the specimen channel, and the bypass channel is connected to said main outlet; and wherein when said bypass valve is in said first position the first outlet of the bypass valve is open and the second outlet of the bypass valve is closed, and when said bypass valve is in said second position the first outlet of the bypass valve is closed and the second outlet of the bypass valve is open.

In some embodiments, the endoscope system further comprises further comprising a fluid container containing a fluid, said fluid container being connectable to said endoscope handle.

According to a seventh aspect the invention relates to a specimen dock for an endoscope system for delivering a fluid to a patient and retrieving for diagnostic purposes from the patient a specimen, said specimen dock being configured to hold a first specimen container, said specimen dock comprising a main inlet for receiving the specimen, a main outlet, a specimen channel having a first specimen outlet and a first suction inlet, and a first specimen valve having a first position and a second position;

wherein said first specimen container has a specimen inlet and a suction outlet, the specimen inlet of the first specimen container is connectable to the first specimen outlet of the specimen dock, the suction outlet of the first specimen container is connectable to the first suction inlet of the specimen dock, the main inlet of the specimen dock is connectable to said endoscope handle, said main outlet of the specimen dock is connectable to said suction device; and wherein said first specimen valve in said first position is configured to guide the specimen flowing in the specimen channel out of said first specimen outlet, and said specimen valve in said second position is configured to block the first specimen outlet and guide the specimen flowing in the specimen channel further downstream in the specimen channel.

According to an eigth aspect the invention relates to use of an endoscope system as disclosed in relation to the sixth aspect or a specimen dock as disclosed in relation to the seventh aspect of the invention for a bronchial lavage (BA) procedure, a bronchoalveolar lavage (BAL) procedure, or a colonoscopy procedure on a human or animal subject.

According to a ninth aspect the invention relates to an endoscope system for delivering a fluid to a patient and retrieving for diagnostic purposes from the patient a specimen, comprising an endoscope, a fluid container containing a fluid, and a first specimen container 103 for receiving a specimen, wherein:

said endoscope comprises a proximal end and a distal end, a handle at the proximal end and an insertion tube extending from the proximal end towards the distal end, the insertion tube comprising an internal working channel extending from the handle to the distal end of the insertion tube;

said fluid container being connectable to said endoscope handle;

said first specimen container being connectable to said endoscope handle and a suction device;

wherein the endoscope system further comprises a connection cable for connecting said endoscope handle with said fluid container and said first specimen container, wherein said connection cable has a proximal end and one or more distal ends, the proximal end being connectable to said endoscope handle and the one or more distal ends being connectable to said fluid container and said first specimen container, wherein said connection cable has a first part extending from said proximal end towards said one or more distal ends, wherein said connection cable comprises a suction channel for connecting the first specimen container with the endoscope handle and a fluid channel for connecting the fluid container with the endoscope handle wherein the suction channel and the fluid channel is connected and forms a multi-lumen cable in said first part of the connection cable.

In some embodiments, the connection cable has a first distal end, a second distal end, and a second part extending from said first part towards the first distal end and the second distal end, wherein the suction channel and the fluid channel splits into a first sub cable and a second sub cable in said second part of the connection cable.

In some embodiments, the connection cable further comprises a one or more signal cables for connecting the endoscope handle with a signal receiving unit, wherein the one or more signal cables are connected to the suction channel and the fluid channel in said first part of the connection cable.

In some embodiments, the signal receiving unit is a display, a storage unit, a communication unit, or a camera unit.

In some embodiments, the connection cable further has a third distal end, the second part extends from said first part towards the first distal end, the second distal end, and the third distal end wherein the suction channel, the fluid channel, and the one or more signal cables splits into a first sub cable, a second sub cable, and a third sub cable in said second part of the connection cable.

In some embodiments, the connection cable is a flexible connection cable adapted to for connecting said endoscope handle with said fluid container and/or said first specimen container arranged remote from said endoscope handle.

According to a tenth aspect the invention relates to a connection cable for use with an endoscope system for delivering a fluid to a patient and retrieving for diagnostic purposes from the patient a specimen, said endoscope system comprising an endoscope, a fluid container containing a fluid, and a first specimen container for receiving a specimen, wherein said endoscope comprises a proximal end and a distal end, a handle at the proximal end and an insertion tube extending from the proximal end towards the distal end, the insertion tube comprising an internal working channel extending from the handle to the distal end of the insertion tube;

said connection cable is configured to connect said endoscope handle with said fluid container and said first specimen container, wherein said connection cable has a proximal end and one or more distal ends, the proximal end being connectable to said endoscope handle and the one or more distal ends being connectable to said fluid container and said first specimen container, wherein said connection cable has a first part extending from said proximal end towards said one or more distal ends, wherein said connection cable comprises a suction channel for connecting the first specimen container with the endoscope handle and a fluid channel for connecting the fluid container with the endoscope handle wherein the suction channel and the fluid channel is connected and forms a multi-lumen cable in said first part of the connection cable.

According to an eleventh aspect the invention relates to use of an endoscope system as disclosed in relation to ninth aspect or a connection cable as disclosed in relation to the tenth aspect according to any one of c a bronchial lavage (BA) procedure, a bronchoalveolar lavage (BAL) procedure, or a colonoscopy procedure on a human or animal subject.

In some embodiments, an opening in the specimen container is adapted such that the distal end of the endoscope's insertion tube can be entered into the specimen container in order to deliver a sample from e.g. the working channel through the distal end of the endoscope. This will be relevant in the event that the working channel, or another channel is blocked e.g. by mucus, phlegm, blood etc. and the material contained in the working channel is needed as a sample. Traditionally such material has been discarded by applying a pressure from the proximal end of the working channel, e.g. by pressing water (or air) into the working channel while placing the distal end of the insertion tube at a sterile cloth or paper. But in the event that it is not possible to obtain another sample, it would be an advantage if the material in the working channel could be collected in a specimen container instead of being discarded.

This can be achieved by entering the distal end of the endoscope into a specimen container and then applying a pressure from the proximal end of the working channel. This may be performed with the specimen container removed from a specimen dock. The opening in the specimen container for this purpose could be an extra opening (not shown in figures), or it could be an existing opening also applied for the connection to the specimen dock. The opening should preferably be self-sealing to avoid spillage of sample material when the tip of the endoscope's insertion tube has been removed. Also, there may be provided an opening for air pressure to escape from the specimen container while the tip of the insertion tube is arranged in the opening. This is to avoid that the applied pressure for removing the blockage from the working channel will also remove the specimen container from the tip of the insertion tube in the moment the blockage passes into the specimen container.

In practice, the operator of the endoscope should remove the insertion tube from the body cavity and from the body as such, when a blockage of the working channel is identified e.g. when suctioning is blocked. The tip of the insertion tube is inserted into the suitable opening in a specimen container, and a pressure source is connected to an entrance to the working channel e.g. at the handle of the endoscope. An increasing air pressure is applied to the working channel, e.g. by the means for instilling saline or alternatively by a syringe, until the blockage is removed and the material from the working channel enters into the sampling container. The tip of the insertion tube is then removed from the specimen container, and may be re-introduced into the body cavity if necessary.

The different aspects of the present invention can be implemented in different ways including as endoscope systems, fluid containers, specimen docks, and connection cables or uses of endoscope systems, fluid containers, specimen docks or connection cables described above and in the following, each yielding one or more of the benefits and advantages described in connection with at least one of the aspects described above, and each having one or more preferred embodiments corresponding to the preferred embodiments described in connection with at least one of the aspects described above and/or disclosed in the dependent claims. Furthermore, it will be appreciated that embodiments described in connection with one of the aspects described herein may equally be applied to the other aspects.

BRIEF DESCRIPTION OF THE DRAWINGS

The above and/or additional objects, features and advantages of the present invention, will be further elucidated by the following illustrative and nonlimiting detailed description of embodiments of the present invention, with reference to the appended drawings, wherein:

FIGS. 3a-c show a schematic drawing of a specimen dock and a specimen container according to an embodiment of the invention, FIG. 4 shows a cross-section of a connection cable according to an embodiment of the invention, FIG. 5a-b show a schematic drawing of a fluid container according to an embodiment of the invention.

DETAILED DESCRIPTION

In the following description, reference is made to the accompanying figures, which show by way of illustration how the invention may be practiced.

Figure 1:
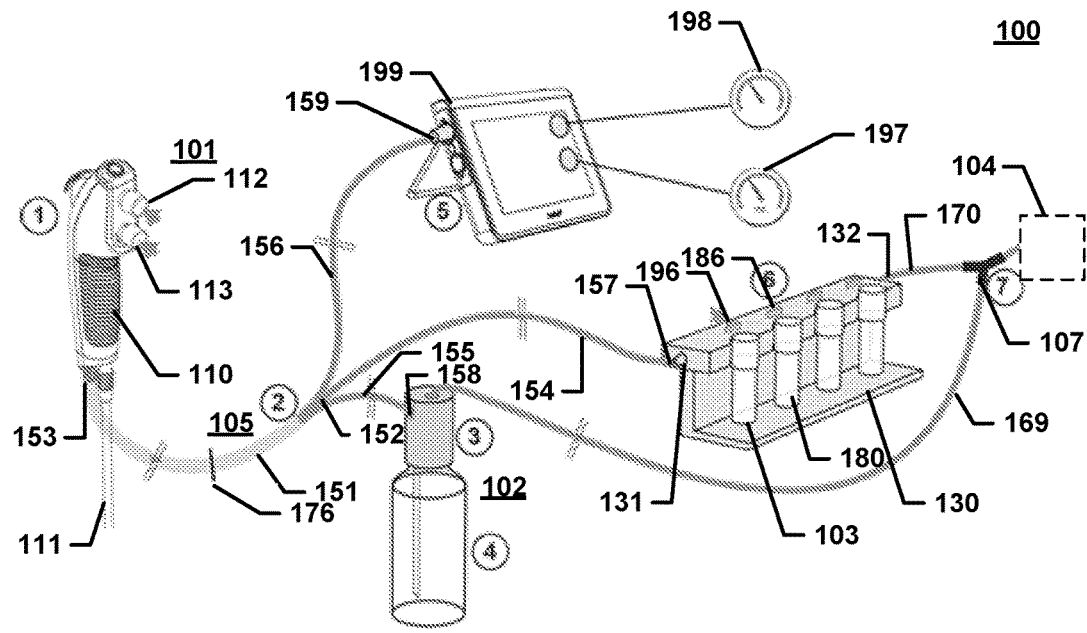
FIG. 1 shows a schematic drawing of an endoscope system according to an embodiment of the invention.
Figure 2:
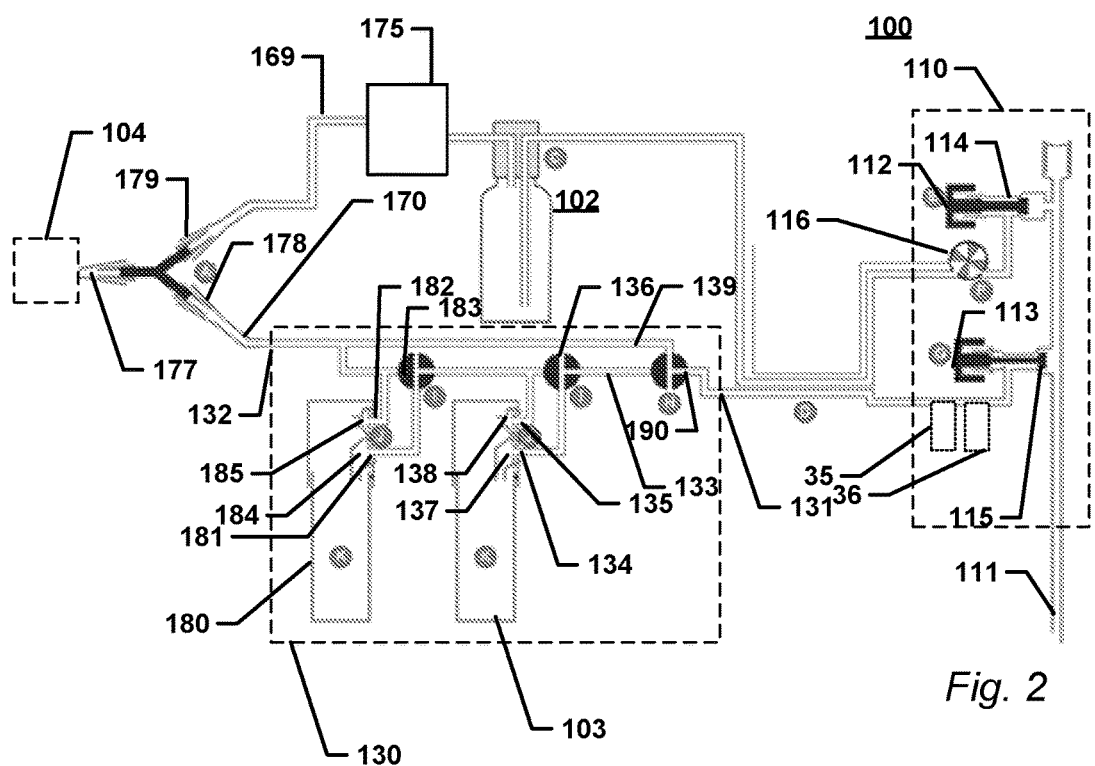
FIG. 2 shows a schematic drawing of an endoscope system according to an embodiment of the invention.

FIGS. 1-2 show schematic drawings of endoscope system for delivering a fluid to a patient and/or retrieving for diagnostic purposes from the patient a specimen according to embodiments of the invention. FIGS. 3a-b show a close-up of a part of FIG. 2. The endoscope system 100 comprises an endoscope 101, a fluid container 102 containing a fluid, and optionally a first specimen container 103 for receiving a specimen. The endoscope 101 comprises a proximal end and a distal end, a handle 110 at the proximal end and an insertion tube 111 extending from the proximal end towards the distal end, the insertion tube 111 comprising an internal working channel extending from the handle 110 to the distal end of the insertion tube 111. Only a part of insertion tube is shown. The fluid container 102 may be connected to the endoscope handle via a connection cable 105. The first specimen container 103 may be connected to the endoscope handle 110 via the connection cable 105 and a specimen dock 130. The first specimen container 103 is further connected to a suction device 104 via a cable 170. In some embodiments the endoscope system 100 has a first user selectable state and a second user selectable state, where the endoscope system 100 in the first user selectable state is configured to automatically deliver the fluid from the fluid container 102 to the patient through the internal working channel and in the second user selectable state is configured to automatically retrieve a specimen through the insertion tube from the patient and provide the specimen to the first specimen container 103.

The endoscope may be an endoscope configured to be introduced in to the airways of a patient, e.g. a bronchoscope. The endoscope system may be adapted for used in procedures such as bronchial lavage (BL), Bronchial wash (BW), or bronchoalveolar lavage (BAL).

The endoscope handle comprises optionally a first button 112 and a second button 113, where the activation of the first button 112 sets the endoscope system in the first user selectable state and the activation of the second button sets said endoscope system in the second user selectable state.

The fluid container 102 may be configured to be pressurized and the handle may comprises a first valve 114 for opening and closing for a fluid flow from the fluid container 102 to the distal opening of the working channel; and a second valve 115 for opening and closing for a fluid flow from the distal end of the working channel to the first specimen container 103, where the activation of the first button 112 opens the first valve 114 and the activation of the second button 113 opens the second valve 115.

The endoscope system 100 may also further comprise one or more flow meters 116 configured to measure the amount of fluid delivered from the fluid container 102 and/or the amount of fluid retrieved from distal end of the working channel.

The endoscope system may further comprise a processing unit and a display 199, where the flow meter 116 is communicatively connectable to the processing unit, and the processing unit is communicatively connectable to the display 199 and configured to control the display 199 to show information related to the amount of fluid delivered 198 and/or retrieved 197. The display may be the same display that is used for displaying images from the distal end of the insertion tube and/or an alternative display e.g. a display arranged on the endoscope handle 110, or simply a few LEDs. The processing unit may further be configured to prevent excessive amounts of fluid from being introduced into the patient e.g. by comparing the amount of fluid delivered with a set maximum level and control an element of the system to prevent further instillation when the set maximum level has been reached. As an example, the processing unit may be communicatively connected to the valve 114, or an element of the fluid container 102 such as a pump and prevent the valve/pump from introducing further fluid once the set maximum level has been reached.

The endoscope system 100 may further comprise a specimen dock 130 configured to hold the first specimen container 103. The specimen dock 130 comprises a main inlet 131 for receiving the specimen, a main outlet 132, a specimen channel 133 having a first specimen outlet 134 and a first suction inlet 135, and a first specimen valve 136 having a first position and a second position. The first specimen container 103 may have a specimen inlet 137 and a suction outlet 138, where the specimen inlet 137 of the first specimen container 103 is connectable to the first specimen outlet 134 of the specimen dock 130, the suction outlet 138 of the first specimen container 103 is connectable to the first suction inlet 135 of the specimen dock 130, the main inlet 131 of the specimen dock 130 is connectable to the endoscope handle 110, the main outlet 132 of the specimen dock 130 is connectable to the suction device 104. The first specimen valve 136 may in the first position be configured to guide the specimen flowing in the specimen channel 133 out of the first specimen outlet 134. The first specimen valve 136 may in the second position be configured to block the first specimen outlet 134 and guide the specimen flowing in the specimen channel 133 further downstream in the specimen channel 133.

The specimen dock 130 may provide a secure place to keep the specimen container limiting the exposure to contagious diseases for the medical personal. The specimen dock further benefits the workflow by eliminating the need for attaching/detaching components (syringes and specimen containers/lukens traps) multiple times throughout the procedure. An additional benefit of eliminating the need for physical interaction with the endoscope handle is reduced risk of compromising wedge position during BAL and general positioning in the airway.

The main inlet 131 of the specimen dock 130 may be connectable to the endoscope handle 110 via a cable 154 connecting the endoscope handle 110 to the main inlet 131 of the specimen dock 130, as shown in FIG. 1. Alternatively, the specimen dock 130 may be directly attached to the endoscope handle 110. The first specimen valve 136 may have an operational element 186 such a knob or a leaver for allowing a user to manually move the specimen valve 136 to the first or the second position.

The specimen channel 133 may be connected to the main inlet 131 and the main outlet 132, the first specimen valve may have an inlet 196, a first outlet 195, and a second outlet 194, where the inlet 196 of the first specimen valve is connected to a first part 193 of the specimen channel, the first outlet of the first specimen valve 195 is connectable to the specimen inlet 137 of the first specimen container 103, the second outlet 194 of the first specimen valve 136 is connected to a second part 192 of the specimen channel 133, and where when the first specimen valve 136 is in the first position (as shown schematically in FIGS. 2 and 3*a*-3*b*) the first outlet 195 of the first specimen valve 136 is open and the second outlet 194 of the first specimen valve 136 is closed, and when the first specimen valve 136 is in the second position the first outlet 195 of the first specimen valve 136 is closed and the second outlet 194 of the first specimen valve 136 is open.

The endoscope system 100 may further comprise a second specimen container 180 connectable to the endoscope handle 110 and the specimen dock 130 may further be configured to hold the second specimen container 180. The specimen channel 133 may further have a second specimen outlet 181, a second suction inlet 182, and a second specimen valve 183 having a first position and a second position. The second specimen container 180 may have a specimen inlet 184 and a suction outlet 185, where the specimen inlet 184 of the second specimen container 180 is connectable to the second specimen outlet 181 of the specimen dock 130, the suction outlet 185 of the second specimen container 180 is connectable to the second suction inlet 182 of the specimen dock 130, and where the second specimen valve 183 in the first position is configured to guide the specimen flowing in the specimen channel 133 downstream from the first specimen valve out of the second specimen outlet 181, and the second specimen valve in the second position is configured to block the second specimen outlet 181 and guide the specimen flowing in the specimen channel 133 further downstream in the specimen channel 133.

Consequently, a plurality of specimens may be collected in a simple and secure manner.

The second specimen valve 183 may have an operational element 186 such a knob or a leaver for allowing a user to manually move the second specimen valve to the first or the second position.

The second specimen valve 183 may be similar to the first specimen valve 136 e.g. the second specimen valve 183 may have an inlet, a first outlet, and a second outlet, the inlet of the second specimen valve 183 being connected to the second part of the specimen channel 192, the first outlet of the second specimen valve 183 is connectable to the specimen inlet 184 of the second specimen container 180, the second outlet of the second specimen valve is connected to a third part of the specimen channel, and where when the second specimen valve 183 is in the first position the first outlet of the second specimen valve 183 is open and the second outlet of the second specimen valve 183 is closed, and when the second specimen valve 183 is in the second position the first outlet of the second specimen valve 183 is closed and the second outlet of the second specimen valve 183 is open.

The specimen dock 130 may be configured to hold more than 2 specimen containers e.g. at least 3 or at least 4 containers. Thus, the specimen dock 130 may comprise a third and a fourth specimen valves. The third and fourth specimen valve may function similar to the first and the second specimen valve 136 183.

The first and/or second specimen container 103 180 may be configured to be attached and detached from the specimen dock in a manner whereby their specimen inlet 137 184 and/or the suction outlet 138 185 is/are configured to automatically close when the first and/or second specimen container 103 180 is detached from the specimen dock to prevent a specimen stored to exit the specimen container 103 108 through the specimen inlet 137 184 and/or the suction outlet 138 185. FIGS. 1, 2 and 3*a*-3*b* shows a specimen dock 130 with specimen containers 103 180 attached and FIG. 3*c* shows specimen container detached from a specimen dock. The specimen inlet 137 may be provided with a flexible closing element 171 having a relaxed state and a compressed/deflected state, where the flexible closing element 171 in the relaxed state (as shown in FIG. 3*c*) is configured to close the specimen inlet 137 to prevent a specimen to exit the specimen container through the specimen inlet 137, and wherein flexible closing element in the compressed/deflected state (as shown in FIGS. 2 and 3*a*-3*b*) is configured to allow a fluid flow through the specimen inlet 137, and wherein the specimen dock is configured to compress/deflect the flexible closing element 171 from the relaxed state to the compressed/deflected state when the specimen container is attached to the specimen dock. As an example the specimen dock may have an extending tube 174 for engaging with the flexible closing element 171 so that when the specimen container is attached to the specimen dock 130 the extending tube compresses the flexible closing element 171 and sets the flexible closing element in the compressed state. Correspondingly, the suction outlet 138 may be provided with a flexible closing element 172 having a relaxed state and a compressed state, where the flexible closing element 172 in the relaxed state (as shown in FIG. 3*c*) is configured to close the suction outlet 138 to prevent a specimen to exit the specimen container through the suction outlet 138, and wherein the flexible closing element 172 in the compressed state (as shown in FIGS. 2 and 3*a*-3*b*) is configured to allow a fluid flow through the suction outlet 138, and wherein the specimen dock is configured to compress the flexible closing element 172 from the relaxed state to the compressed state when the specimen container is attached to the specimen dock. As an example, the specimen dock may have an extending tube 173 for engaging with the flexible closing element 172 so that when the specimen container is attached to the specimen dock 130 the extending tube compresses the flexible closing element 172 and sets the flexible closing element 172 in the compressed state. The flexile closing elements 171 172 may be made of a resilient material such a rubber or rubber like material.

The specimen dock 130 may further comprise a bypass channel 139 and a bypass valve 190 having a first position and a second position, where the bypass valve 190 in the first position is configured to guide the specimen through the bypass channel 139 and out of the main outlet, and the bypass valve 190 in the second position is configured to guide the specimen into the specimen channel 133.

Consequently, the medical personal may in an easy and safe manner control the point in time when a specimen is taken. This further enable the medical personal in an easy manner to remove body fluids from a patient for non-diagnostic purposes.

The bypass valve 190 may have an operational element such as a knob or a leaver for allowing a user to move the valve to the first or the second position.

The bypass valve 190 may have an inlet, a first outlet, and a second outlet, where the inlet of the bypass valve 190 is connected to the main inlet 131, the first outlet of the bypass valve is connected to the bypass channel 139, the second outlet of the bypass valve is connected to the first part of the specimen channel 193, and the bypass channel 139 is connected to the main outlet 132, where when the bypass valve 139 is in the first position (as shown in FIG. 3*b*) the first outlet of the bypass valve is open and the second outlet of the bypass valve 190 is closed, and when the bypass valve 190 is in the second position (as shown in FIG. 3*a*) the first outlet of the bypass valve is closed and the second outlet of the bypass valve is open.

The endoscope system 100 may further comprise a pump 175 configured to draw air into the fluid container 102 through an air inlet of the fluid container thereby creating over pressure in the fluid container 102 that can be used to propel the fluid stored in the fluid container 102 out of a fluid outlet of the fluid container 102 and into a patient via the endoscope handle 110. The pump 175 may be configured to use the suction device 104 as an energy source but it may also use other alternative energy sources e.g. the pump 175 may be configured to use electrical energy.

The endoscope system 100 may further comprise a connection cable 105 for connecting the endoscope handle 110 with the fluid container 102 and the first specimen container 103, where the connection cable 105 has a proximal end 153 and one or more distal ends, the proximal 153 end being connectable to the endoscope handle 110 and the one or more distal ends being connectable to the fluid container 102 and the first specimen container 103. FIG. 4 shows a cross-section of the connection cable 105 at the line 176 shown in FIG. 1. The connection cable 105 may have a first part 151 extending from the proximal end 153 towards the one or more distal ends, wherein the connection cable 105 comprises a suction channel 154 for connecting the first specimen container 103 with the endoscope handle 110 and a fluid channel 155 for connecting the fluid container 102 with the endoscope handle 110 wherein the suction channel 154 and the fluid channel 155 is connected and forms a multi-lumen cable in the first part 151 of the connection cable 105. This makes it easier to setup the endoscope system 100 for use. Furthermore, by having a multi-lumen cable the number of cables connected to the endoscope handle 110 may be reduced thereby making movement of the endoscope less restricted.

The connection cable 105 has a first distal end 157, a second distal end 158, and a second part 152 extending from the first part 151 towards the first distal end 157 and the second distal end 158, wherein the suction channel 154 and the fluid channel 155 splits into a first sub cable and a second sub cable in the second part 152 of the connection cable 105.

The connection cable 105 may further comprise one or more signal cables 156 for connecting the endoscope handle 110 with a signal receiving unit such as a display 199. The one or more signal cables 156 may be connected to the suction channel 154 and the fluid channel 155 in the first part 151 of the connection cable 105. The connection cable may further comprise one or more power cables e.g. a power cables for providing power to a camera arranged at the distal end of the insertion tube.

The connection cable 105 may further have a third distal end 159, and wherein the second part 152 extends from the first part 151 towards the first distal end 157, the second distal end 158, and the third distal end 159 where the suction channel 154, the fluid channel 155, and the one or more signal cables 156 splits into a first sub cable, a second sub cable, and a third sub cable in the second part 152 of the connection cable 105.

The endoscope system may further comprise a suction splitter 107 having a suction outlet 177, a first suction inlet 178 and a second suction inlet 179, where the suction outlet 177 is connected to the suction device 104 optionally via a cable, the first suction inlet is connectable to the first specimen container 103 via a cable 170 and the second suction inlet is connected to the suction outlet 127 of the second chamber 122 of the fluid container 102 via a cable 169.

The endoscope system 100 may optionally have a suction reduction valve 35, with which the operator can reduce the amount of suction provided by the vacuum source, and a manometer or other pressure indicator 36. The pressure indicator 36, if provided, is preferably located in a position of the endoscope system 100 where, in use, it is visible by the operator.

It should be noted though, that the pressure indicator 36 is just a further option, and that the suction reduction valve 35 may be implemented without the pressure indicator 36, and in principle also vice versa. The pressure indicator 36 need not be able to give a detailed reading. Rather, it is envisaged that a simple indication that the pressure is within an acceptable range may suffice.

Both the suction reduction valve 35 and the pressure indicator 36 are schematically shown in FIG. 2 as forming part of the endoscope handle. However, they may be provided on other parts of the system e.g. the specimen dock 130.

The actual nature and design of the suction reduction valve 35 may be one of many. It could be a throttling valve adjustable with a screw or similar. It could also be a slider covering one or more openings through which false air may be drawn in to reduce the suction pressure. This could be one long opening that is gradually covered, or several smaller holes covered one by one in steps. Especially in case where false air is relied on for suction pressure reduction, the suction reduction valve is preferably arranged between an external connector to the suction device 104 and the last specimen container of the specimen dock, in order not to draw the false air from the ambient air in the environment through a specimen container, as this would potentially be a cause for pollution of the sample with pollutants from the ambient environment, which were never in the lungs of the patient. Also, if the latter solution with false air is used, the pressure indicator 36 is preferably located between the suction reduction valve 35 and the endoscope handle or in the endoscope handle 110 in order to ensure correct reading of the pressure indicator 36. An actuator may be arranged in connection with the suction reduction valve 35 and configured to control the suction reduction valve 35 in response to activation of a control element communicatively coupled to the actuator e.g. a physical button on the endoscope handle or a button on a touch screen. This may allow the user to control the suction reduction valve 35 in an easy manner even when the suction reduction valve 35 is not arranged on the endoscope handle 110 .

FIGS. 5a-b show a schematic drawing of a fluid container 102 containing a fluid 126 according to an embodiment of the invention, where FIG. 5a shows a side view and FIG. 5b shows a central cross-section. The fluid container 102 has a first chamber 121 and a second chamber 122, a turbine 123, a fan 124, and a mechanical coupling 125. The fluid 126 is stored in the first chamber 121, the second chamber 122 is sealed off from the first chamber 121, the mechanical coupling 125 couples the turbine 123 with the fan 124 so that a rotation of the turbine 123 results in a rotation of the fan 124. The second chamber 121 has an air inlet and a suction outlet 127, the suction outlet 127 is connectable to a suction device, the turbine 123 is arranged in the air inlet and configured to rotate when air is flowing through the air inlet into the second chamber 122. The first chamber 121 has an air inlet and a fluid outlet 128. The fluid outlet 128 is connectable to an endoscope handle, the fan 124 is arranged in the air inlet and configured to draw air into the first chamber 121 when being rotated. Thus, when the suction outlet 127 is connected to a suction device an under pressure is created in the second chamber 122 drawing air into the second chamber through the air inlet resulting in a rotation of the turbine 123 and through the mechanical coupling 125 a rotation of the fan 124, the rotation of the fan 124 draws air into the first chamber 121 creating an over pressure in the first chamber 121. The over pressure may be used to propel the fluid 126 stored in the first chamber 121 out of the fluid outlet 128 and into the patient via the endoscope handle.

Consequently, a suction device such as the wall suction present in most hospital operating rooms may be used as an energy source to propel the fluid 126 from the fluid container 102. The fluid container 102 comprises a bottom element 160 and a top element 161, the top element 161 comprises the second chamber 122, the fan 124 and the turbine 123, the top element 161 being connectable to the bottom element 160, and the top element 161 and the bottom element 160 together forms the first chamber 121.

Consequently, by having most of the complex parts of the fluid container in the top element, the bottom element may be exchanged if more fluid is needed. As an example the bottom element may be a standard saline container used as part of a normal clinical practice.

The top element 161 may further comprise a suction channel 129 having a proximal end, a distal end, and a suction channel fluid inlet 162. The distal end of the suction channel 129 is adapted to extend into the fluid 126 stored in the first chamber 121. The suction channel fluid inlet 162 being formed at the distal end of the suction channel 129 and the fluid outlet 128 of the first chamber 121 being formed at the proximal end of said suction channel 129.

Although some embodiments have been described and shown in detail, the invention is not restricted to them, but may also be embodied in other ways within the scope of the subject matter defined in the following claims. In particular, it is to be understood that other embodiments may be utilized and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

Further embodiments of the invention are disclosed in the below enumerated embodiments.

1. An endoscope system 100 for bronchial lavage (BL) or bronchoalveolar lavage (BAL), comprising an endoscope 101, a fluid container 102 containing a fluid, and a first specimen container 103 for receiving a specimen, wherein:

said endoscope 101 comprises a proximal end and a distal end, a handle 110 at the proximal end and an insertion tube 111 extending from the proximal end towards the distal end, the insertion tube 111 comprising an internal working channel extending from the handle to the distal end of the insertion tube 111;

said fluid container 102 being connectable to said endoscope handle;

said first specimen container 103 being connectable to said endoscope handle 110 and a suction device 104;

wherein the endoscope system further comprises a connection cable 105 for connecting said endoscope handle 110 with said fluid container 102 and said first specimen container 103, wherein said connection cable 105 has a proximal end 153 and one or more distal ends, the proximal 153 end being connectable to said endoscope handle 110 and the one or more distal ends being connectable to said fluid container 102 and said first specimen container 103, wherein said connection cable 105 has a first part 151 extending from said proximal end 153 towards said one or more distal ends, wherein said connection cable 105 comprises a suction channel 154 for connecting the first specimen container 103 with the endoscope handle 110 and a fluid channel 155 for connecting the fluid container 102 with the endoscope handle 110 wherein the suction channel 154 and the fluid channel 155 is connected and forms a multi-lumen cable in said first part 151 of the connection cable 105.

2. An endoscope system according to embodiment 1, wherein the connection cable 105 has a first distal end 157, a second distal end 158, and a second part 152 extending from said first part 151 towards the first distal end 157 and the second distal end 158, wherein the suction channel 154 and the fluid channel 155 splits into a first sub cable and a second sub cable in said second part 152 of the connection cable 105.

3. An endoscope system according to embodiment 2, wherein the connection cable 105 further comprises a one or more signal cables 156 for connecting the endoscope handle 110 with a signal receiving unit 199, wherein the one or more signal cables 156 are connected to the suction channel 54 and the fluid channel 155 in said first part 151 of the connection cable 105.

4. An endoscope system according to embodiment 3, wherein the signal receiving unit is a display, a storage unit, a communication unit, or a camera unit.

5. An endoscope system according to embodiments 3 or 4, wherein the connection cable 105 further has a third distal end 159, the second part 1052 extends from said first part 151 towards the first distal end 157, the second distal end 158, and the third distal end 159 wherein the suction channel 154, the fluid channel 155, and the one or more signal cables 156 splits into a first sub cable, a second sub cable, and a third sub cable in said second part 152 of the connection cable 105.

6. A connection cable for use with an endoscope system 100 for delivering a fluid to a patient and retrieving for diagnostic purposes from the patient a specimen, said endoscope system comprising an endoscope 101, a fluid container 102 containing a fluid, and a first specimen container 103 for receiving a specimen, wherein said endoscope 101 comprises a proximal end and a distal end, a handle 110 at the proximal end and an insertion tube 111 extending from the proximal end towards the distal end, the insertion tube 111 comprising an internal working channel extending from the handle to the distal end of the insertion tube 111;

said connection cable is configured to connect said endoscope handle 110 with said fluid container 102 and said first specimen container 103, wherein said connection cable 105 has a proximal end 153 and one or more distal ends, the proximal 153 end being connectable to said endoscope handle 110 and the one or more distal ends being connectable to said fluid container 102 and said first specimen container 103, wherein said connection cable 105 has a first part 151 extending from said proximal end 153 towards said one or more distal ends, wherein said connection cable 105 comprises a suction channel 154 for connecting the first specimen container 103 with the endoscope handle 110 and a fluid channel 155 for connecting the fluid container 102 with the endoscope handle 110 wherein the suction channel 154 and the fluid channel 155 is connected and forms a multi-lumen cable in said first part 151 of the connection cable 105.

7. Use of an endoscope system according to any one of embodiments 1 to 5 or a connection cable according to embodiment 6 for a bronchial lavage (BA) procedure, a bronchoalveolar lavage (BAL) procedure, or a colonoscopy procedure on a human or animal subject.

8. An endoscope system 100 for bronchial lavage (BL) or bronchoalveolar lavage (BAL), comprising an endoscope 101, and a first specimen container 103 for receiving a specimen, wherein:

said endoscope 101 comprises a proximal end and a distal end, a handle 110 at the proximal end and an insertion tube 111 extending from the proximal end towards the distal end, the insertion tube 111 comprising an internal working channel extending from the handle to the distal end of the insertion tube 111;

said first specimen container 103 being connectable to said endoscope handle 110 and a suction device 104;

wherein said endoscope system 100 further comprising a specimen dock 130 configured to hold said first specimen container 103, said specimen dock 130 comprising a main inlet 131 for receiving the specimen, a main outlet 132, a specimen channel 133 having a first specimen outlet 134 and a first suction inlet 135, and a first specimen valve 136 having a first position and a second position;

wherein said first specimen container 103 has a specimen inlet 137 and a suction outlet 138, the specimen inlet 137 of the first specimen container 103 is connectable to the first specimen outlet 134 of the specimen dock, the suction outlet 138 of the first specimen container is connectable to the first suction inlet 135 of the specimen dock, the main inlet 131 of the specimen dock is connectable to said endoscope handle, said main outlet 132 of the specimen dock is connectable to said suction device 104; and wherein said first specimen valve 136 in said first position is configured to guide the specimen flowing in the specimen channel 133 out of said first specimen outlet 134, and said specimen valve in said second position is configured to block the first specimen outlet 134 and guide the specimen flowing in the specimen channel 133 further downstream in the specimen channel 133.

9. An endoscope system according to embodiment 8, wherein said specimen channel is connected to said main inlet and said main outlet, the first specimen valve has an inlet, a first outlet, and a second outlet, the inlet of the first specimen valve is connected to a first part of the specimen channel, the first outlet of the first specimen valve is connectable to the specimen inlet of the first specimen container, the second outlet of the first specimen valve is connected to a second part of the specimen channel, and wherein when said first specimen valve is in said first position the first outlet of the first specimen valve is open and the second outlet of the first specimen valve is closed, and when said first specimen valve is in said second position the first outlet of the first specimen valve is closed and the second outlet of the first specimen valve is open.

10. An endoscope system according to embodiments 8 or 9, further comprising a second specimen container connectable to said endoscope handle, said specimen dock being further configured to hold said second specimen container, said specimen channel further have a second specimen outlet, a second suction inlet, and a second specimen valve having a first position and a second position;

wherein said second specimen container has a specimen inlet and a suction outlet, the specimen inlet of the second specimen container is connectable to the second specimen outlet of the specimen dock, the suction outlet of the second specimen container is connectable to the second suction inlet of the specimen dock, and wherein said second specimen valve in said first position is configured to guide the specimen flowing in the specimen channel downstream from said first specimen valve out of said second specimen outlet, and said specimen valve in said second position is configured to block the second specimen outlet and guide the specimen flowing in the specimen channel further downstream in the specimen channel.

11. An endoscope system according to embodiment 10, wherein the second specimen valve has an inlet, a first outlet, and a second outlet, the inlet of the second specimen valve is connected to the second part of the specimen channel, the first outlet of the second specimen valve is connectable to the specimen inlet of the second specimen container, the second outlet of the second specimen valve is connected to a third part of the specimen channel, and wherein when said second specimen valve is in said first position the first outlet of the second specimen valve is open and the second outlet of the second specimen valve is closed, and when said second specimen valve is in said second position the first outlet of the second specimen valve is closed and the second outlet of the second specimen valve is open.

12. An endoscope system according to any one of embodiments 8 to 11, wherein said first specimen container can be attached and detached from said specimen dock, and wherein said specimen inlet and/or said suction outlet is/are configured to automatically close when said first specimen container is detached from said specimen dock to prevent a specimen stored in said specimen container to exit said specimen container through said specimen inlet and/or said suction outlet.

13. An endoscope system according to any one of embodiments 8 to 5, said specimen dock further comprises a bypass channel 139 and a bypass valve 190 having a first position and a second position;

wherein said bypass valve 190 in said first position is configured to guide the specimen through the bypass channel 139 and out of the main outlet, and said bypass valve 190 in said second position is configured to guide the specimen into said specimen channel 133.

14. An endoscope system according to embodiment 13, wherein said bypass valve has an inlet, a first outlet, and a second outlet, the inlet of the bypass valve is connected to said main inlet, the first outlet of the bypass valve is connected to the bypass channel, the second outlet of the bypass valve is connected to the first part of the specimen channel, and the bypass channel is connected to said main outlet; and wherein when said bypass valve is in said first position the first outlet of the bypass valve is open and the second outlet of the bypass valve is closed, and when said bypass valve is in said second position the first outlet of the bypass valve is closed and the second outlet of the bypass valve is open.

15. An endoscope system according to any one of embodiments 8 to 14, further comprising a fluid container 102 containing a fluid, said fluid container 102 being connectable to said endoscope handle.

16. A specimen dock 130 for an endoscope system 100 for delivering a fluid to a patient and retrieving for diagnostic purposes from the patient a specimen, said specimen dock being configured to hold a first specimen container 103, said specimen dock 130 comprising a main inlet 131 for receiving the specimen, a main outlet 132, a specimen channel 133 having a first specimen outlet 134 and a first suction inlet 135, and a first specimen valve 136 having a first position and a second position;

wherein said first specimen container 103 has a specimen inlet 137 and a suction outlet 138, the specimen inlet 137 of the first specimen container 103 is connectable to the first specimen outlet 134 of the specimen dock, the suction outlet 138 of the first specimen container is connectable to the first suction inlet 135 of the specimen dock, the main inlet 131 of the specimen dock is connectable to said endoscope handle, said main outlet 132 of the specimen dock is connectable to said suction device 104; and wherein said first specimen valve 136 in said first position is configured to guide the specimen flowing in the specimen channel 133 out of said first specimen outlet 134, and said specimen valve in said second position is configured to block the first specimen outlet 134 and guide the specimen flowing in the specimen channel 133 further downstream in the specimen channel 133.

17. Use of an endoscope system according to any one of embodiments 8 to 15 or a specimen dock according to embodiment 16 for a bronchial lavage (BA) procedure, a bronchoalveolar lavage (BAL) procedure, or a colonoscopy procedure on a human or animal subject.

18. An endoscope system 100 for delivering a fluid to a patient, comprising an endoscope 101, a fluid container 102 containing a fluid, wherein:

said endoscope 101 comprises a proximal end and a distal end, a handle 110 at the proximal end and an insertion tube 111 extending from the proximal end towards the distal end, the insertion tube 111 comprising an internal working channel extending from the handle to the distal end of the insertion tube 111;

said fluid container 102 being connectable to said endoscope handle;

wherein said endoscope system 100 has a first user selectable state, wherein said endoscope system 100 in said first user selectable state is configured to automatically deliver the fluid from said fluid container 102 to the patient through said internal working channel.

19. An endoscope system according to embodiment 18, wherein said endoscope handle comprises a first button 112, and wherein the activation of said first button 112 sets said endoscope system in said first user selectable state.

20. An endoscope system according to embodiments 18 or 19, wherein said fluid container is configured to be pressurized.

21. An endoscope system according to embodiment 20, said handle comprises a first valve 114 for opening and closing for a fluid flow from said fluid container to the distal opening of said working channel; and wherein the activation of said first button 112 opens said first valve 114.

22. An endoscope system according to embodiments 20 or 21, wherein the endoscope system further comprises a pump configured to draw air into the fluid container through an air inlet of the fluid container thereby creating over pressure in said fluid container that can be used to propel the fluid stored in said first chamber 121 out of a fluid outlet of the fluid container and into a patient via the endoscope handle.

23. An endoscope system according to embodiments 21 or 22, wherein said fluid container 102 has a first chamber 121 and a second chamber 122, a turbine 123, a fan 124, and a mechanical coupling 125, wherein said fluid 126 is stored in said first chamber 121, said second chamber 122 being sealed off from said first chamber 121, said mechanical coupling 125 couples said turbine 123 with said fan 124 so that a rotation of said turbine 123 results in a rotation of said fan 124, wherein said second chamber 121 has an air inlet and a suction outlet 127, said suction outlet 127 being connectable to a suction device, said turbine 123 being arranged in said air inlet and being configured to rotate when air is flowing through said air inlet into said second chamber 122, said first chamber 121 having an air inlet and a fluid outlet 128, wherein said fluid outlet 128 is connectable to the endoscope handle, said fan 124 is arranged in said air inlet and being configured to draw air into the first chamber when being rotated, whereby when said suction outlet 127 is connected to said suction device an under pressure is created in said second chamber 122 drawing air into said second chamber through said air inlet resulting in a rotation of said turbine 123 and through said mechanical coupling 125 a rotation of said fan 124, the rotation of said fan 124 drawing air into said first chamber 121 creating an over pressure in said first chamber 121 that can be used to propel the fluid 126 stored in said first chamber 121 out of said fluid outlet 128 and into the patient via the endoscope handle.

24. An endoscope system according to embodiment 23, wherein said fluid container 102 comprises a bottom element 160 and a top element 161, the top element 161 comprising said second chamber 122 and said turbine 123, said top element 161 being connectable to said bottom element 160, and said top element 161 and said bottom element 160 together forms said first chamber 121.

25. An endoscope system according to embodiment 24, wherein said top element 161 further comprises said fan 124.

26. An endoscope system according to embodiment 25, wherein said fluid container 102 further comprises a suction channel 129 having a proximal end, a distal end, and a suction channel fluid inlet 162, wherein the distal end of the suction channel 129 is adapted to extend into said fluid 126 stored in said first chamber 121, said suction channel fluid inlet 162 being formed at said distal end of the suction channel 129 and the fluid outlet 128 of the first chamber 121 being formed at said proximal end of said suction channel 129.

27. A fluid container for use with an endoscope system for delivering a fluid to a patient, wherein said fluid container 102 has a first chamber 121 and a second chamber 122, a turbine 123, a fan 124, and a mechanical coupling 125, wherein said fluid 126 is stored in said first chamber 121, said second chamber 122 being sealed off from said first chamber 121, said mechanical coupling 125 couples said turbine 123 with said fan 124 so that a rotation of said turbine 123 results in a rotation of said fan 124, wherein said second chamber 121 has an air inlet and a suction outlet 127, said suction outlet 127 being connectable to a suction device, said turbine 123 being arranged in said air inlet and being configured to rotate when air is flowing through said air inlet into said second chamber 122, said first chamber 121 having an air inlet and a fluid outlet 128, wherein said fluid outlet 128 is connectable to an endoscope handle of said endoscope system, said fan 124 is arranged in said air inlet and being configured to draw air into the first chamber when being rotated, whereby when said suction outlet 127 is connected to said suction device an under pressure is created in said second chamber 122 drawing air into said second chamber through said air inlet resulting in a rotation of said turbine 123 and through said mechanical coupling 125 a rotation of said fan 124, the rotation of said fan 124 drawing air into said first chamber 121 creating an over pressure in said first chamber 121 that can be used to propel the fluid 126 stored in said first chamber 121 out of said fluid outlet 128 and into a patient via the endoscope handle.

28. Use of an endoscope system according to any one of embodiments 18 to 26 or a fluid container according to embodiment 27 for a bronchial lavage (BA) procedure, a bronchoalveolar lavage (BAL) procedure, or a colonoscopy procedure on a human or animal subject.

The invention claimed is:
1. An endoscope system for bronchial lavage (BL) or bronchoalveolar lavage (BAL), the endoscope system comprising an endoscope, a fluid container containing a fluid, and a first specimen container for receiving a specimen, wherein:
  said endoscope comprises a proximal end and a distal end, a handle at the proximal end and an insertion tube extending from the proximal end towards the distal end, the insertion tube comprising an internal working channel extending from the handle to the distal end;
  said fluid container operable to establish fluid communication with said endoscope handle:
  said first specimen container operable to establish fluid communication with said endoscope handle and with a suction device; and
  said endoscope system has a first user selectable state and a second user selectable state, wherein said endoscope system in said first user selectable state is configured to automatically deliver the fluid from said fluid container to the patient through said internal working channel and in said second user selectable state is configured to automatically retrieve a specimen from the patient through said insertion tube and provide the specimen to said first specimen container,
  wherein the endoscope system further comprises a specimen dock configured to hold said first specimen container, said specimen dock comprising a main inlet for receiving the specimen, a main outlet, a specimen channel having a first specimen outlet and a first suction inlet, and a first specimen valve having a first position and a second position;
  wherein said first specimen container has a specimen inlet and a suction outlet, the specimen inlet of the first specimen container is connectable to the first specimen outlet of the specimen channel, the suction outlet of the first specimen container is connectable to the first suction inlet of the specimen channel, the main inlet of the specimen dock is connectable to said endoscope handle, and said main outlet of the specimen dock is connectable to said suction device; and
  wherein said first specimen valve in said first position is configured to establish fluid communication between the main inlet and the first specimen outlet to guide the specimen to said first specimen outlet, and said first specimen valve in said second position is configured to block fluid communication between the main inlet and the first specimen outlet and to establish fluid communication between the main inlet and a downstream portion of the specimen channel to guide the specimen to the downstream portion of the specimen channel.

2. The endoscope system of claim 1, wherein said specimen channel is connected to said main inlet and said main outlet, the first specimen valve has an inlet, a first outlet, and a second outlet, the inlet of the first specimen valve is connected to a first part of the specimen channel, the first outlet of the first specimen valve is connectable to the specimen inlet of the first specimen container, and the second outlet of the first specimen valve is connected to a second part of the specimen channel, and wherein when said first specimen valve is in said first position the first outlet of the first specimen valve is open and the second outlet of the first specimen valve is closed, and when said first specimen valve is in said second position the first outlet of the first specimen valve is closed and the second outlet of the first specimen valve is open.

3. The endoscope system of claim 1, wherein the endoscope system further comprises a second specimen container, said specimen dock being further configured to hold said second specimen container, said specimen channel further comprising a second specimen outlet, a second suction inlet, and a second specimen valve having a first position and a second position;

wherein said second specimen container has a specimen inlet and a suction outlet, the specimen inlet of the second specimen container is connectable to the second specimen outlet of the specimen channel, the suction outlet of the second specimen container is connectable to the second suction inlet of the specimen channel, and wherein said second specimen valve in said first position is configured to guide the specimen flowing in the specimen channel downstream from said first specimen valve and out of said second specimen outlet, and said specimen valve in said second position is configured to block flow to the second specimen outlet and guide the specimen flowing in the specimen channel further downstream in the specimen channel.

4. The endoscope system of claim 3, wherein the second specimen valve has an inlet, a first outlet, and a second outlet, the inlet of the second specimen valve is connected to the second part of the specimen channel, the first outlet of the second specimen valve is connectable to the specimen inlet of the second specimen container, and the second outlet of the second specimen valve is connected to a third part of the specimen channel, and wherein when said second specimen valve is in said first position the first outlet of the second specimen valve is open and the second outlet of the second specimen valve is closed, and when said second specimen valve is in said second position the first outlet of the second specimen valve is closed and the second outlet of the second specimen valve is open.

5. The endoscope system of claim 1, wherein said first specimen container can be attached and detached from said specimen dock, and wherein said specimen inlet and/or said suction outlet is/are configured to automatically close when said first specimen container is detached from said specimen dock to prevent a specimen stored in said specimen container to exit said specimen container through said specimen inlet and/or said suction outlet.

6. The endoscope system of claim 1, wherein said specimen dock further comprises a bypass channel and a bypass valve having a first position and a second position;

wherein said bypass valve in said first position is configured to guide the specimen through the bypass channel and out of the main outlet, and bypass valve in said second position is configured to guide the specimen into said specimen channel.

7. The endoscope system of claim 6, said bypass valve has an inlet, a first outlet, and a second outlet, the inlet of the bypass valve is connected to said main inlet, the first outlet of the bypass valve is connected to the bypass channel, the second outlet of the bypass valve is connected to the first part of the specimen channel, and the bypass channel is connected to said main outlet; and wherein when said bypass valve is in said first position the first outlet of the bypass valve is open and the second outlet of the bypass valve is closed, and when said bypass valve is in said second position the first outlet of the bypass valve is closed and the second outlet of the bypass valve is open.

8. An endoscope system for bronchial lavage (BL) or bronchoalveolar lavage (BAL), the endoscope system comprising an endoscope, a fluid container containing a fluid, and a first specimen container for receiving a specimen, wherein:

said endoscope comprises a proximal end and a distal end, a handle at the proximal end and an insertion tube extending from the proximal end towards the distal end, the insertion tube comprising an internal working channel extending from the handle to the distal end;

said fluid container operable to establish fluid communication with said endoscope handle:

said first specimen container operable to establish fluid communication with said endoscope handle and with a suction device; and said endoscope system has a first user selectable state and a second user selectable state, wherein said endoscope system in said first user selectable state is configured to automatically deliver the fluid from said fluid container to the patient through said internal working channel and in said second user selectable state is configured to automatically retrieve a specimen from the patient through said insertion tube and provide the specimen to said first specimen container, wherein said fluid container has a first chamber and a second chamber, a turbine, a fan, and a mechanical coupling, wherein said fluid is stored in said first chamber, said second chamber being sealed off from said first chamber, said mechanical coupling couples said turbine with said fan so that rotation of said turbine results in rotation of said fan, wherein said second chamber has an air inlet and a suction outlet, said suction outlet being connectable to a suction device, said turbine being arranged in said air inlet and being configured to rotate when air is flowing through said air inlet into said second chamber, said first chamber having an air inlet and a fluid outlet, wherein said fluid outlet is connectable to the endoscope handle, said fan is arranged in said air inlet and being configured to draw air into the first chamber when being rotated, whereby when said suction outlet is connected to said suction device an under pressure is created in said second chamber drawing air into said second chamber through said air inlet resulting in rotation of said turbine and through said mechanical coupling rotation of said fan, the rotation of said fan drawing air into said first chamber creating an over pressure in said first chamber that can be used to propel the fluid stored in said first chamber out of said fluid outlet and into the patient via the endoscope handle.

9. The endoscope system of claim 8, wherein said endoscope handle comprises a first button and activation of said first button sets said endoscope system in said first user selectable state or said second user selectable state.

10. The endoscope system of claim 8, wherein said endoscope handle comprises the first button and a second button, and wherein the activation of said first button sets said endoscope system in said first user selectable state and activation of said second button sets said endoscope system in said second user selectable state.

11. The endoscope system of claim 10, wherein said internal working channel has a distal opening, wherein said fluid container is configured to be pressurized, wherein said handle comprises a first valve for opening and closing a fluid flow from said fluid container to the distal opening of said internal working channel and a second valve for opening and closing a fluid flow from said distal opening of said internal working channel to said first specimen container, and wherein the activation of said first button opens said first valve and the activation of said second button opens said second valve.

12. The endoscope system of claim 8, wherein the endoscope system further comprises a pump configured to draw air into the fluid container through an air inlet of the fluid container thereby creating over pressure in said fluid container that can be used to propel the fluid stored in said first chamber out of a fluid outlet of the fluid container and into a patient via the endoscope handle.

13. The endoscope system of claim 8, wherein said fluid container comprises a bottom element and a top element, the top element comprising said second chamber and said turbine, said top element being connectable to said bottom element, and said top element and said bottom element together form said first chamber.

14. The endoscope system of claim 13, wherein said top element further comprises said fan.

15. The endoscope system of claim 8, wherein said fluid container further comprises a suction channel having a proximal end, a distal end, and a suction channel fluid inlet,
wherein the distal end of the suction channel is adapted to extend into said fluid stored in said first chamber, said suction channel fluid inlet being formed at said distal end of the suction channel and the fluid outlet of the first chamber being formed at said proximal end of said suction channel.

16. The endoscope system of claim 8, wherein the endoscope system further comprises a connection cable for connecting said endoscope handle with said fluid container and said first specimen container, wherein said connection cable has a proximal end and one or more distal ends, the proximal end being connectable to said endoscope handle and the one or more distal ends being connectable to said fluid container and said first specimen container, wherein said connection cable has a first part extending from said proximal end towards said one or more distal ends, wherein said connection cable comprises a suction channel for connecting the first specimen container with the endoscope handle and a fluid channel for connecting the fluid container with the endoscope handle, wherein the suction channel and the fluid channel are connected and form a multi-lumen cable in said first part of the connection cable.

17. The endoscope system of claim 16, wherein the connection cable has a first distal end, a second distal end, and a second part extending from said first part towards the first distal end and the second distal end, wherein the suction channel and the fluid channel splits into a first sub cable and a second sub cable in said second part of the connection cable.

18. The endoscope system of claim 16, wherein the connection cable further comprises a one or more signal cables, wherein the one or more signal cables are connected to the suction channel and the fluid channel in said first part of the connection cable.

19. The endoscope system of claim 18, wherein the connection cable further has a third distal end, the second part extends from said first part towards the first distal end, the second distal end, and the third distal end, wherein the suction channel, the fluid channel, and the one or more signal cables splits into a first sub cable, a second sub cable, and a third sub cable in said second part of the connection cable.

20. The endoscope system of claim 8, wherein the endoscope system further comprises a suction splitter having a suction outlet, a first suction inlet and a second suction inlet, wherein the suction outlet is connectable to the suction device, the first suction inlet is connectable to the first specimen container and the second suction inlet is connectable to the suction outlet of the second chamber of the fluid container.

21. Use of an endoscope system according to claim 8 for a bronchial lavage (BA) procedure, a bronchoalveolar lavage (BAL) procedure, or a colonoscopy procedure on a human or animal subject.

\* \* \* \* \*